United States Patent [19]

Ellman et al.

[11] 4,182,037

[45] Jan. 8, 1980

[54] HONING STONE ATTACHMENT FOR DENTAL HANDPIECE

[76] Inventors: Allen Ellman, 1 Auerbach La., Lawrence, N.Y. 11516; Jon Garito, 22 Deering La., East Rockaway, N.Y. 11558

[21] Appl. No.: 920,321

[22] Filed: Jun. 29, 1978

[51] Int. Cl.² ............................................. A61C 1/08
[52] U.S. Cl. ..................................... 433/110; 433/125
[58] Field of Search .................. 51/3, 170 PT, 181 R; 32/27, 26, 59, 23, 40 R

[56] References Cited

U.S. PATENT DOCUMENTS

| 881,691 | 3/1908 | Hughes | 32/59 |
| 2,323,665 | 7/1943 | Clausen | 32/23 |

*Primary Examiner*—Robert Peshock

[57] ABSTRACT

A honing stone attachment for a low-speed dental handpiece is described. The lock rod for the handpiece, which is used to close and open the chuck for receiving burs, is provided at its rear with a honing stone. Operation of the handpiece causes the honing stone to rotate, which makes readily available for the dentist a sharpening instrument for his tools.

4 Claims, 3 Drawing Figures

U.S. Patent
Jan. 8, 1980
4,182,037
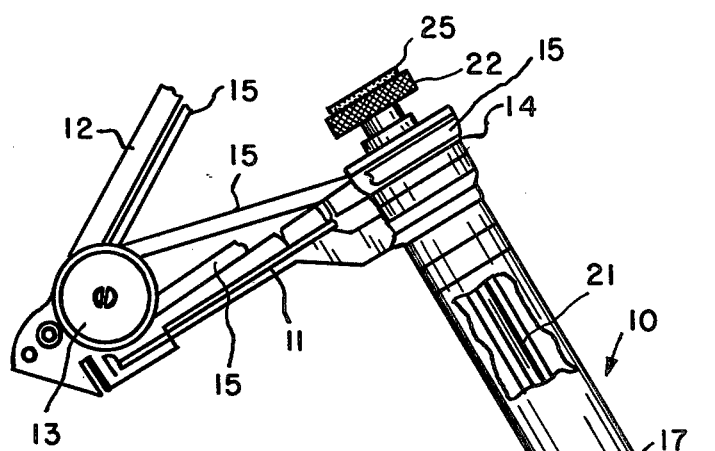
Fig. 1
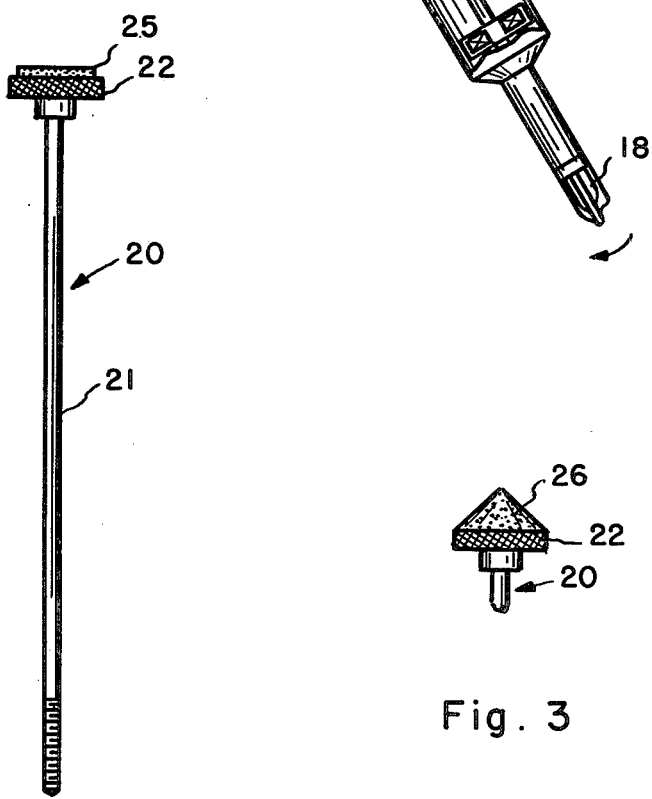
Fig. 2
Fig. 3

HONING STONE ATTACHMENT FOR DENTAL HANDPIECE

This invention relates to a dental sharpening tool, and also to a sharpening attachment for a low-speed dental handpiece.

The traditional low-speed straight handpiece is still used by dentists for various dental purposes. By "low-speed" dental handpiece is meant the well-known belt-driven straight handpiece which employs a lock rod operable at the rear to tighten and loosen the chuck at the forward end which is adapted to receive burs or brushes. Should the dentist need to sharpen or refurbish one of his instruments, such as a scaler or the like, he must leave the patient in order to bring the instrument to a sharpening device.

The chief object of the invention is to make available a simple sharpening tool near the patient to save time.

This object is achieved by providing an attachment that can be added to a low-speed dental handpiece. In particular, a honing stone or like abrasive device is secured to the lock rod of the dental handpiece. When it is driven by the usual belt and pulley system, the honing stone rotates, thus making available near the patient, chair side, a suitable sharpening tool for the dentist's instruments.

The invention will now be described in greater detail with respect to the accompanying drawings, wherein:

FIG. 1 shows the assembled handpiece with one embodiment of the sharpening attachment of the invention in place;

FIG. 2 shows the lock rod attachment used in the embodiment of FIG. 1;

FIG. 3 shows a modified honing stone.

Referring now to the drawings, FIG. 1 is a view of the handpiece end of a conventional belt-driven low-speed dental equipment. The handpiece, indicated generally at 10, is suspended in the usual manner on a set of pivotable arms, only two of which are shown at 11 and 12. Pulleys are provided where the arms pivot, one of which is shown at 13. The handpiece 10 also has a pulley 14 at its upper end. On the pulleys 13, 14 is provided a belt 15. When the belt 15 is driven by means, not shown, the pulley 14 on the handpiece 10 is rotated.

The handpiece 10, which, except for the modified lock rod, is of a standard type well known in the art, comprises a straight elongated cylindrical housing 17 which at its forward end is provided with a chuck 18 adapted to receive the shank of a usual bur or brush. The chuck 18 is actuated by a lock rod 20, which comprises a straight shaft 21 threaded at its lower end for mounting purposes, and which extends from the chuck 18 throughout the length of the housing 17. At the remote end the lock rod 20 terminates in a knurled nut 22. There is a locking nut under the pulley which secures the lock rod 20 in position within the handpiece in the usual manner. Rotation of the knurled end 22 actuates the chuck 18. By releasing the lock nut, the lock rod may be unscrewed and removed from the handpiece 10. When the belt 15 is actuated, the lock rod 20 and knurled end 22 are also rotated together with the chuck 18.

In accordance with the invention, a sharpening tool is mounted, as by gluing or other fastening means, on the knurled nut 22. In the embodiment shown in FIGS. 1 and 2, the sharpening tool is a flat abrasive disc 25. In the modification of FIG. 3, it is a conical abrasive stone 26. Other shapes and configurations of abrasive surfaces to serve as honing stones for sharpening or refurbishing of different instruments can also be used in place of the disc and conical stones illustrated in the drawings.

When the handpiece is operated utilizing the conventional variable speed control, the abrasive stone 25 can be rotated at various speeds and used by the dentist to quickly and efficiently sharpen his instruments right at the patient's chair, thus enabling the dentist to work faster, save valuable time, and lengthen the life of his instruments.

The handpiece 10 of the invention illustrated in FIG. 1 can be sold to dentists with the honing stone 25 mounted in position as shown. Alternatively, just the modified lock rod 20 of the invention illustrated in FIG. 2 can be sold to dentists, who can then use same as an attachment to replace the standard lock rod of their conventional handpiece and thus make readily available a sharpening instrument as above described. As a further alternative, a set of replacement lock rods each with a different shaped sharpening device attached to the knurled end can be furnished to the dentist, who can then employ whichever shaped sharpening instrument is best suited for the procedure planned. A suitable set could include, for example, diamond abrasives configured flat, round, and conically inward, i.e., with an inverted radius. These configurations allow the top as well as the sides of the hones to be used for sharpening or reshaping surgical, carbon and stainless steel dental tools. As still a further alternative, cleaning devices can be mounted on the knurled end of the lock rod, for example, steel bristles for cleaning burs, diamonds, and stones of acrylics, composites and cements, or soft bristles for removing debris from dentures.

While our invention has been described in connection with specific embodiments thereof, those skilled in the art will recognize that various modifications are possible within the principles enunciated herein and thus the present invention is not to be limited to the specific embodiments disclosed.

What is claimed is:

1. A sharpening attachment for use with a low-speed dental handpiece having a chuck at one end operable by a threaded lock rod, comprising a straight rod having a lower threaded portion at one end adapted to engage the chuck and a knurled member at the opposite end for actuating the chuck, and an abrasive member secured to the knurled member, said rod being adapted to mount within said dental handpiece for operative connection to and rotable with said chuck when the latter is driven.

2. The attachment of claim 1 wherein the abrasive member is a honing stone.

3. A low-speed dental handpiece having a chuck at one end for receiving a threaded lock rod for actuating the chuck, a belt-driven pulley at the opposite end, a lock rod mounted within the handpiece and having a threaded end operatively connected to the chuck for actuating same, said lock rod having a knurled end protruding from the opposite end of the handpiece, and a honing stone mounted on the knurled end and rotatable therewith when the pulley is driven.

4. A cleaning attachment for use with a low speed dental handpiece having a chuck at one end operable by a threaded lock rod, comprising a straight rod having a lower threaded portion at one end adapted to engage the chuck and a knurled member at the opposite end for actuating the chuck, and a cleaning bristled member secured to the knurled member, said rod being adapted to mount within said dental handpiece for operative connection to and rotatable with the chuck when the latter is driven.

* * * * *